(12) United States Patent
Gustafsson et al.

(10) Patent No.: US 6,610,902 B1
(45) Date of Patent: Aug. 26, 2003

(54) ABSORBENT STRUCTURE FOR USE IN AN ABSORBENT ARTICLE

(75) Inventors: Anders Gustafsson, Billdal (SE); Ted Guidotti, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/297,583

(22) PCT Filed: Nov. 11, 1997

(86) PCT No.: PCT/SE97/01883
§ 371 (c)(1),
(2), (4) Date: Aug. 3, 1999

(87) PCT Pub. No.: WO98/22059
PCT Pub. Date: May 28, 1998

(30) Foreign Application Priority Data

Nov. 15, 1996 (SE) ................................................ 9604226

(51) Int. Cl.⁷ ............................. A61F 13/15; A61F 13/20
(52) U.S. Cl. ........................................ 604/378; 604/367
(58) Field of Search ................................. 604/367, 378, 604/385.01, 385.101

(56) References Cited

U.S. PATENT DOCUMENTS

| | | |
|---|---|---|
| 810,119 A | 1/1906 | Green |
| 810,120 A | 1/1906 | Green |
| 810,131 A | 1/1906 | Green |
| 1,946,626 A | 2/1934 | Jurgensen |
| 2,551,663 A | 5/1951 | Fox |
| 3,407,814 A | 10/1968 | George et al. |
| 3,468,311 A | 9/1969 | Gallagher |
| 3,570,493 A | 3/1971 | Olsson |
| 3,888,255 A | 6/1975 | Shah et al. |
| 4,041,950 A | 8/1977 | Jones, Jr. |
| 4,047,531 A * | 9/1977 | Karami .................... 128/290 |
| 4,195,634 A | 4/1980 | DiSalvo et al. |
| 4,217,901 A | 8/1980 | Bradstreet et al. |
| 4,351,340 A | 9/1982 | McLeod |
| 4,386,932 A | 6/1983 | Pitts |

(List continued on next page.)

FOREIGN PATENT DOCUMENTS

| | | |
|---|---|---|
| EP | 0 067 377 A2 | 12/1982 |
| EP | 0 155 515 A1 | 9/1985 |
| EP | 0 155 515 B1 | 9/1985 |

(List continued on next page.)

OTHER PUBLICATIONS

U.S. patent application Ser. No. 09/297,366, filed Jul. 7, 1999; Inventors: Anette Johansson et al. (WO 98/22060).
U.S. patent application Ser. No. 09/297,365, filed Aug. 2, 1999; Inventors: Camilla Björklund et al. (WO 98/22057).
U.S. patent application Ser. No. 09/297,584, filed Aug. 12, 1999, Inventors: Camilla Björklund et al. (WO 98/22058).
U.S. patent application Ser. No. 09/297,637, filed Aug. 12, 1999; Inventors: Camilla Björklund et al. (WO 98/22061).
U.S. patent application Ser. No. 09/297,746, filed Sep. 1, 1999; Inventors, Ann Samuelsson et al. (WO 98/22062).

*Primary Examiner*—Weilun Lo
*Assistant Examiner*—Michele Kidwell
(74) *Attorney, Agent, or Firm*—Burns, Doane, Swecker & Mathis L.L.P.

(57) ABSTRACT

An absorbent structure for use in an absorbent article such as a diaper, an incontinence guard, a sanitary napkin, or the like wherein the absorbent structure has two different material types, which are in direct or indirect contact with each other so that liquid can be transferred between the material types. The first material type is constituted by material which swells when absorbing body fluid and the second material type is constituted by material which collapses when absorbing body fluid, wherein the volume increase in the first material type is essentially equal to the volume reduction in the second material type when the absorbent structure is saturated with liquid, whereby the absorbent structure has substantially the same volume both in a wet and in a dry state.

12 Claims, 3 Drawing Sheets

U.S. PATENT DOCUMENTS

| | | |
|---|---|---|
| 4,536,181 A | 8/1985 | Cook |
| 4,643,726 A | 2/1987 | Gegelys |
| 4,673,403 A | 6/1987 | Lassen et al. |
| 4,804,380 A | 2/1989 | Lassen et al. |
| 4,828,555 A | 5/1989 | Hermansson |
| 4,846,824 A | 7/1989 | Lassen et al. |
| 4,865,597 A | 9/1989 | Mason, Jr. et al. |
| 4,897,084 A | 1/1990 | Ternström et al. |
| 4,911,701 A | 3/1990 | Mavinkurve |
| 5,032,121 A | 7/1991 | Mokry |
| 5,074,855 A | 12/1991 | Rosenbluth et al. |
| 5,074,856 A | 12/1991 | Coe et al. |
| 5,080,658 A | 1/1992 | Igaue et al. |
| 5,098,422 A | 3/1992 | Davis et al. |
| 5,114,419 A | 5/1992 | Daniel et al. |
| 5,129,893 A | 7/1992 | Thorén |
| 5,171,302 A | 12/1992 | Buell |
| 5,181,563 A | 1/1993 | Amaral |
| 5,197,959 A | 3/1993 | Buell |
| 5,295,987 A | 3/1994 | Widlund et al. |
| 5,354,400 A | 10/1994 | Lavash et al. |
| 5,374,260 A | 12/1994 | Lemay et al. |
| 5,383,868 A | 1/1995 | Hyun |
| 5,454,802 A | 10/1995 | Lindquist et al. |
| 5,460,623 A | 10/1995 | Emenaker et al. |
| 5,545,156 A | 8/1996 | DiPalma et al. |
| 5,558,656 A | 9/1996 | Bergman |
| 5,569,231 A | 10/1996 | Emenaker et al. |
| 5,591,150 A * | 1/1997 | Olsen et al. ............ 604/385.1 |
| H1634 H | 2/1997 | Oetjen et al. |
| 5,624,421 A | 4/1997 | Dabi et al. |
| 5,688,259 A | 11/1997 | Osborn, III et al. |
| 5,695,324 A | 12/1997 | Weirich |
| 5,704,931 A | 1/1998 | Holtman et al. |
| 5,722,967 A | 3/1998 | Coles |
| 5,741,241 A * | 4/1998 | Guidotti et al. ............ 604/368 |
| 5,827,258 A | 10/1998 | McFall et al. |
| 5,849,003 A | 12/1998 | Olsen et al. |
| 5,873,869 A | 2/1999 | Hammons et al. |
| 5,919,178 A * | 7/1999 | Widlund ............ 604/368 |
| 5,957,909 A | 9/1999 | Hammons et al. |
| 5,961,508 A | 10/1999 | Mayer et al. |
| 6,020,536 A * | 2/2000 | Osterdahl et al. ............ 604/378 |
| 6,033,391 A | 3/2000 | Osborne, III et al. |
| 6,042,575 A | 3/2000 | Osborn, III et al. |
| 6,080,909 A * | 6/2000 | Osterdahl et al. ............ 604/368 |

FOREIGN PATENT DOCUMENTS

| | | | |
|---|---|---|---|
| EP | 0 235 763 A1 | 9/1987 | |
| EP | 0 248 173 A1 | 12/1987 | |
| EP | 0 335 252 A2 | 10/1989 | |
| EP | 0 335 253 A1 | 10/1989 | |
| EP | 0 335 253 B1 | 10/1989 | |
| EP | 0 336 578 A1 | 10/1989 | |
| EP | 0 339 041 B1 | 11/1991 | |
| EP | 0 606 082 A1 | 7/1994 | |
| EP | 0 419 434 B2 | 11/1998 | |
| FR | 2 694 187 | 1/1994 | |
| GB | 2 119 656 | 11/1983 | |
| GB | 2 119 657 | 11/1983 | |
| WO | 92/19197 | 11/1992 | |
| WO | 93/15702 | 8/1993 | |
| WO | 93/21879 | 11/1993 | |
| WO | 94/10956 * | 5/1994 | ............ A61F/13/15 |
| WO | 95/31165 | 11/1995 | |
| WO | 96/20679 | 7/1996 | |
| WO | 96/26699 | 9/1996 | |
| WO | 97/09015 | 3/1997 | |
| WO | 98/22058 | 5/1998 | |

* cited by examiner

ABSORBENT STRUCTURE FOR USE IN AN ABSORBENT ARTICLE

TECHNICAL FIELD

The invention relates to an absorbent structure intended for use in an absorbent article such as a sanitary napkin, a diaper, or an incontinence guard, whereby the absorbent structure comprises two different material types which are in direct or indirect contact, so that liquid may be transferred between the material types.

BACKGROUND OF THE INVENTION

When manufacturing an absorbent article of the above-mentioned kind, it is often desirable to be able to provide the article with a three-dimensional shape which is adapted to the anatomy of the user of the article. By designing an absorbent article so that it follows and conforms to the body shape of the user, a number of advantages are namely achieved, such as increased comfort for the user, increased leakage-security and improved discretion, i.e. the article may more easily be concealed underneath the clothing of the user.

An obvious difficulty in connection with the shaping of an absorbent article is, however, that the shape of the article changes during use. The deformation is particularly obvious after wetting of the article. Cellulose fluff pulp is an absorbent material which is often used in absorbent articles. Cellulose fluff pulp is a readily available and comparatively cheap absorbent material which, for example by means of air-laying, may be relatively easily utilized in order to give an absorbent article a desired shape. A considerable disadvantage with cellulose fluff pulp is, however, that the material collapses when it is wetted and loses its original shape. An absorbent article with an absorbent structure manufactured from cellulose fluff pulp will consequently only maintain an original, three-dimensional shape in an initial stage, before the article has absorbed body fluid.

Another disadvantage with absorbent structures which consist of cellulose fluff pulp is that they have a reduced volume after wetting. This implies that the fibre structure within the wet region has thinner capillaries than surrounding dry fibre material. Thus, liquid distribution in the absorbent structure is counteracted so that the liquid for the most part remains in the initially wetted region of the structure. This region is therefore rapidly saturated with liquid and is thereafter unable to absorb additional liquid which is emitted to the absorbent structure. As a consequence, there is a large risk that the liquid, instead of penetrating into the absorbent structure, flows out over the surface on the absorbent article and causes leakage.

The problem with insufficient shape permanence of absorbent articles is particularly obvious in connection with sanitary napkins and other absorbent articles which have a proportionately small size and which are intended to be worn inside a pair of ordinary panties. Since such articles of necessity are fairly narrow, leakage of body fluid out past the longitudinal side edges of the article is not an untypical problem. Such leakage is of course highly undesired, since it entails the risk of soiling the clothing of the user. Due to the rather short extension of the article in the longitudinal direction, it is furthermore not unusual that liquid also leaks out forwards and backwards, past the end edges of the article. Rearwards-leakage is a particular problem which, as a rule, arises when the user is lying down, for example during the night.

One way of reducing the risk of edge leakage caused by deformation of the article during use is to provide the article with a pre-formed hump which, during use, is intended to be in contact with the genitals of the user. In this way, excreted body fluid may be caught as soon as it exits the body of the user, and immediately absorbed into the article without flowing out over the surface thereof.

Previously known absorbent articles provided with a liquid-receiving hump are, however, afflicted with a number of disadvantages.

A common way of creating a hump has been to simply build it up by means of arranging a larger quantity of absorbent material within the region of the hump. Since the most commonly used absorbent material is cellulose fluff pulp, such a hump collapses and loses its shape when it is wetted. In order to obtain a hump which is also sufficiently large in a wet state, a hump consisting of cellulose fluff pulp has to comprise so much absorbent material that is becomes far too high, hard and uncomfortable to wear in a dry state.

In order to solve the problem with large, hard and uncomfortable humps, it has been suggested in EP 0 339 041 to provide the liquid-impervious surface of the article with transverse elastic members. Such elastic members impart a certain resiliency to the article in case it is subjected to flattening. However, the elastic members do not to any great extent prevent the hump from being compressed and from changing shape during use.

In another publication, EP 0 419 434, it has been suggested to create a soft hump on an absorbent article by means of locking the side edges of the article at a mutual distance which is smaller than the planar distance between the side edges. Neither does this known article, however, retain its shape during use.

In EP 0 335 252 and EP 0 335 253 it has been suggested to provide an absorbent article with a deformation element. The deformation element is influenced by the transverse compressive forces between the thighs of a user. The purpose of the deformation element is that, during use, it creates a bulge in a portion of the article in a direction towards the body of the user. However, it is impossible to completely control, or predict the shape the article will adopt for each individual user. Furthermore, it is not possible to ensure contact between the body of the user and the surface of the article, since the degree of bulging is completely determined by how much the article is compressed in the transverse direction.

Accordingly, there remains a need for a leakage-proof absorbent article which has a predictable shape, both before and during use, and which maintains its shape independently of the wetting the article is subjected to.

An article designed according to the invention and of the type mentioned in the introduction, is primarily characterized in that the first material type is constituted by material which swells when absorbing body fluid, and the second material type is constituted by material which collapses when absorbing body fluid, whereby the volume increase in the first material type is essentially as large as the volume reduction in the second material type when the absorbent structure is saturated with liquid, whereby the absorbent structure has substantially the same volume both in both a wet and a dry state.

By ensuring that the volume of the absorbent structure is practically constant, independently of whether the structure is dry or wet, according to the invention it is possible to provide absorbent articles with very good shape permanence.

BRIEF DESCRIPTION OF THE DRAWINGS

In the following, the invention will be described in greater detail with reference to the figures which are shown in the attached drawings. Thus.

DETAILED DESCRIPTION OF PREFERRED EMBODIMENTS

Figure 1:
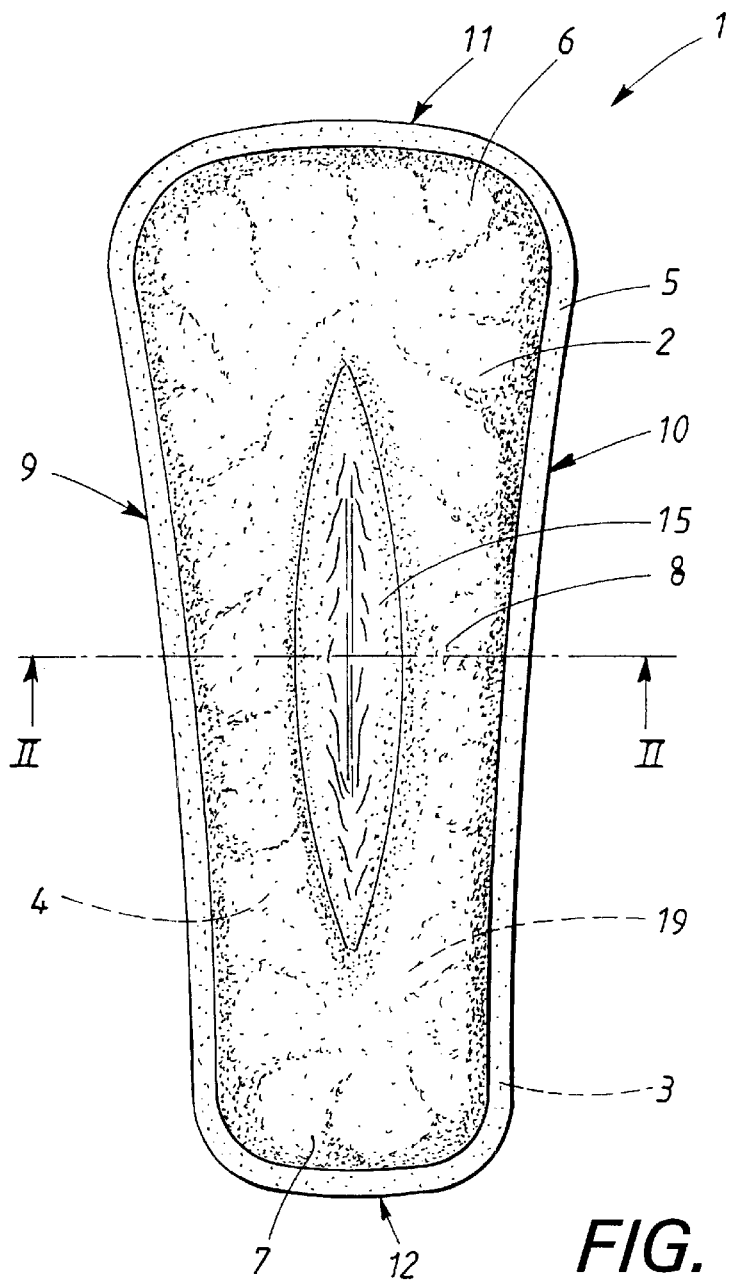
FIG. 1 shows a plan view of a sanitary napkin in accordance with the invention, seen from the side facing the user during use.
Figure 2:
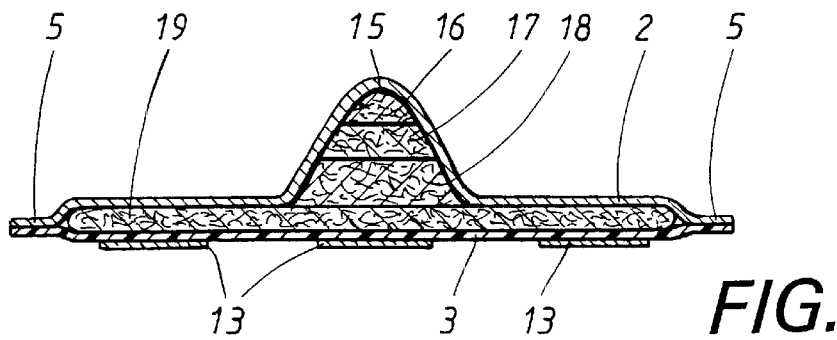
FIG. 2 shows a section along line II—II through the sanitary napkin of FIG. 1.

The sanitary napkin 1, shown in FIGS. 1 and 2, comprises a liquid-pervious cover layer 2, arranged on the side of the sanitary napkin 1 which during use is intended to be facing the user. The liquid-pervious cover layer 2 suitably consists of a soft, skin-friendly material. Examples of useful liquid-pervious cover materials are different types of non-woven fibre fabrics, so-called nonwoven materials. Other liquid-pervious cover materials are perforated plastic films, scrims, knitted, crocheted or woven textiles, and combinations and laminates of the listed material types.

The sanitary napkin 1 further comprises a liquid-impervious cover layer 3, arranged on the side of the sanitary napkin 1 which during use is intended to be facing away from the user. Usually, a thin plastic film is used as a liquid-impervious cover layer 3. However, it is also possible to use liquid-pervious material layers which are coated with a liquid-impervious material. Other treatments, such as thermo-calendering for fusing an initally liquid-pervious material into a substantially liquid-impervious layer, may also be utilized. Furthermore, it is possible to use nonwoven materials, or other textiles which are sufficiently dense, and the fibres of which are sufficiently hydrophobic, so that they may serve as a liquid barrier layer.

The two cover layers 2, 3 are mutually interconnected around an absorbent body 4 and form a projecting connection line 5 around the periphery of the sanitary napkin. The connection between the cover layers 2, 3 may be achieved using any technique suitable for the purpose, such as gluing, welding, or sewing.

The sanitary napkin 1 has a trapezoid-shape, with a wider front portion 6, a narrower rear portion 7, and an intermediate centre portion 8. Furthermore, the sanitary napkin 1 has two oblique side edges 9, 10, which extend between two almost straight end edges 11, 12.

An adhesive attachment member 13 is arranged as three glue stripes extending in the longitudinal direction of the sanitary napkin 1 on the liquid-impervious cover layer 3.

An elongated hump 15 is arranged centrally in the longitudinal direction of the sanitary napkin 1. The hump 15 is widest at the centre portion 8 of the sanitary napkin and tapers in a direction towards the front and rear portions 6, 7. Furthermore, it is convenient if the hump 15 is profiled in the longitudinal direction so that it is highest at the centre portion 8 and gradually decreases in height in a direction towards the end portions 6, 7.

The hump 15 constitutes a part of the absorbent body 4 and is built up from three parts of absorbent material, whereby a first part 16, arranged immediately inside the liquid-pervious cover layer 2, consists of absorbent material which collapses during wetting. On the inner side of the first part 16, seen in a direction from the liquid-pervious cover layer 2, there is provided a second part 17 consisting of absorbent material which swells when wetted. Finally, a third part 18, consisting of absorbent material which collapses when wetted, is arranged on the inner side of the second part 17, between the second part and an absorbent layer 19, which is part of the absorbent body 4.

Naturally, it is conceivable within the scope of the invention that the hump 15 is constituted by only two parts, whereof one collapses when wetted and the other swells when wetted. Furthermore, the absorbent structure in the hump 15 may optionally be constituted by a plurality of material layers which alternatingly consist of swelling and collapsing materials. In a hump 15 constituted by layers with alternating properties, the absorbent structure may advantageously be arranged so that the layers stand erect, substantially perpendicularly to the absorbent layer 19 arranged on the inner side of the hump 15. Thereby, simultaneous wetting of both swelling and collapsing material is achieved, which implies that the shape stability of the hump 15 becomes especially good.

The absorbent layer 19 primarily constitutes a safety zone around the central hump 15. Secondly, it serves as extra absorption capacity which may be utilized if the absorbent material in the hump 15 is saturated by unexpectedly large liquid quantities. Furthermore, the absorbent layer 19 contributes to providing the sanitary napkin 1 with a planar extension, so that the sanitary napkin 1 may be attached inside a pair of panties by means of the attachment member 13, arranged on the liquid-impervious cover layer 3.

The first part 16 of the hump 15 may for example consist of one or several material layers of air-laid latex-bonded paper with a low density, cellulose fluff pulp, tissue-layers, cotton, rayon, or the like. What is required is that the material in the first part 16 collapses when wetted e.g., when absorbing a liquid such as a bodily fluid, so that the volume and thickness of the first part 16 are reduced.

A suitable material for the second part 17, which is located between the first part 16 and the third part 18, is the absorbent material which is disclosed in WO 94/10956. This material is a dry-formed fibre layer with high density and stiffness, which is used directly in an absorbent article without first being defibered. Another useful similar material, with especially suitable properties for blood absorption purposes, is disclosed in WO 94/10953. The materials disclosed in WO 94/10956 and WO 94/10953 have very good absorption capacity and swell in the thickness direction when they absorb liquid.

Another useful category of absorbent materials, with the ability to swell during absorption, are so-called super-absorbents. Super-absorbent materials refer to polymers which are present in the form of fibres, flakes, particles, granular material, or the like and which may absorb several times their own weight of body fluid during swelling and formation of a gel. The super-absorbent material may be applied as an unbonded layer between the first part 16 and the third part 18, or be bonded or blended into a fibre structure.

The second part 17 may be constituted by a homogenous body, or may consist of two or more layers of swelling absorbent material.

The third part 18 in the hump 15, as well as the first part 16, consist of absorbent material which collapses during wetting. Suitable absorbent materials are those which are listed in connection with the first part 16.

TEST METHOD

In order to determine whether an absorbent material collapses or swells during liquid absorption, the height of a material sample was measured before and after wetting, under two different loads.

Procedure: Cylindrical samples of the tested absorbent material, with a diameter of 50 mm, were punched out.

A sample is placed standing on one of its circular surfaces in a bowl with a perforated base, whereafter the upper surface of the sample, i.e. the second circular surface, is loaded with a weight. The height of the cylindrical sample is measured and noted.

Thereafter, the sample is allowed to absorb synthetic menstrual fluid from below by means of lowering the bowl with the perforated base into a liquid container, and maintaining the perforated base below the liquid level in the container until liquid is detected on the upper surface of the sample. The height of the sample is measured and noted once again.

EXAMPLE 1

Five samples, each consisting of four layers of one and the same absorbent material, were punched out for two different material types: a) and b)

Material-type a) was a latex-bonded, air-laid cellulose fibre material with a basis weight of 80 g/m$^2$, a layer thickness of 1.18 mm and a density of 68 g/m$^3$. Such materials are provided commercially by a number of different suppliers.

Material-type b) was an unbonded dry-formed cellulose fibre material of the type which is disclosed in WO 94/10953 and WO 94/10956. These materials have high density and stiffness and are used directly in an absorbent article, without preceding defibration. In the present example, the basis weight of the material was 350 g/m$^2$, the layer thickness 0.9 mm and the density 390 g/m$^3$.

Measurements of the sample height were performed at a load of 500 g, and with a load of 150 g. Both material-types, a) and b) were tested in a wet and dry state, respectively. The results from the measurements are shown in FIG. 3.

Figure 3:
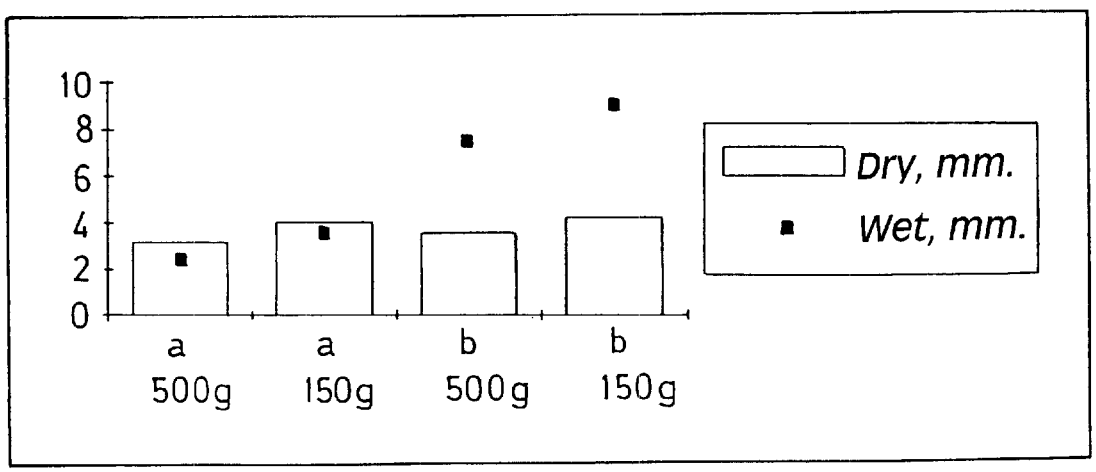
FIG. 3 shows a diagram of the results from the test measurements of both material types a) and b) using wet and dry samples.

As is evident from FIG. 3, material-type a) collapses less under the lower load than under the higher load. In a corresponding way, the expansion for material-type b) is slightly smaller when the sample is loaded with the larger weight. Inter alia, this implies that in an absorbent body containing both material-type a) and material-type b), material-type b) may during expansion to some extent displace material-type a).

EXAMPLE 2

Seven different samples, consisting of different combinations of material type a) and material type b), were prepared as follows:
I: 6 layers a), 1 layer b), 6 layers a)
II: 5 layers a), 1 layer b), 5 layers a)
III: 4 layers a), 1 layer b), 4 layers a)
IV: 3 layers a), 1 layer b), 3 layers a)
V: 3 layers a), 1 layer b), 2 layers a)
VI: 2 layers a), 1 layer b), 2 layers a)
VII: 2 layers a), 1 layer b), 1 layer a)

Figure 4:
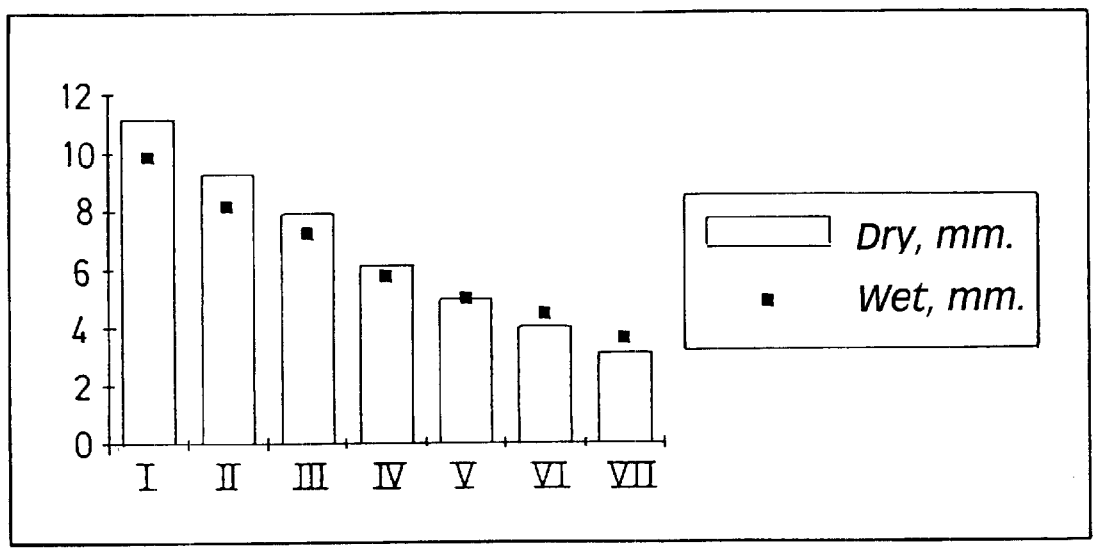
FIG. 4 shows a diagram of the height in mm for samples I–VII in both wet and dry states.

The height in mm for the different samples I–VII was recorded both in a wet and in a dry state, under a load of 500 g. The results from the measurements can be derived from FIG. 4.

Figure 5:
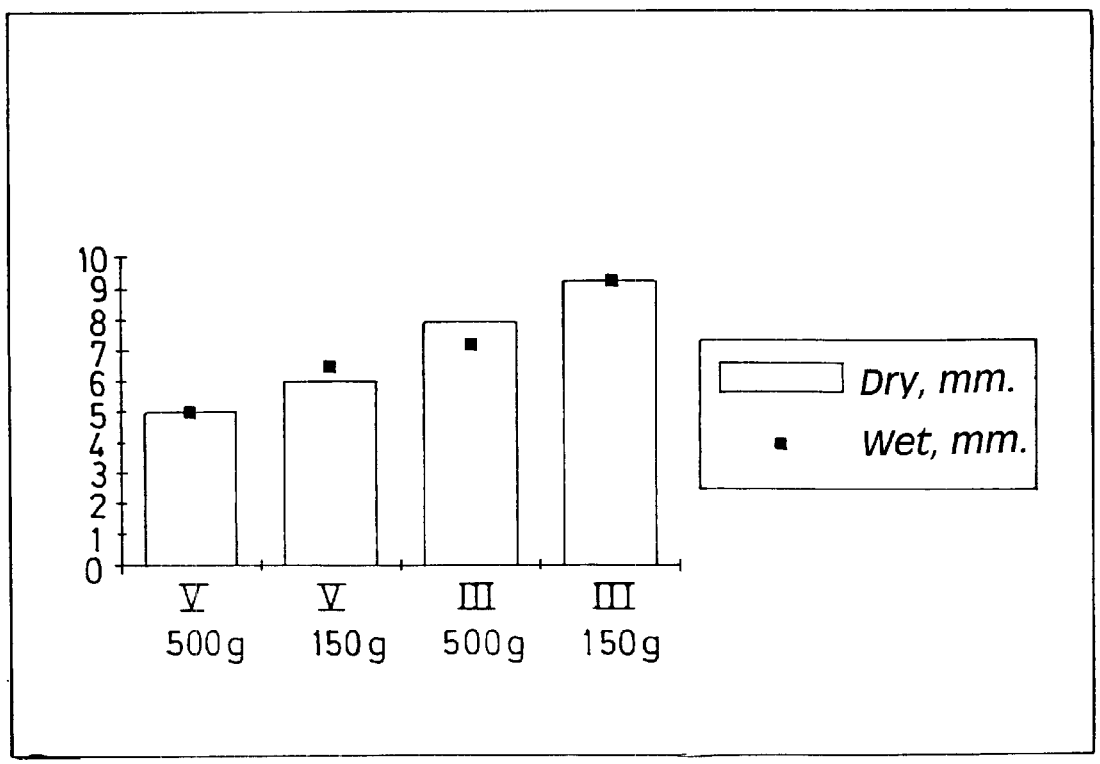
FIG. 5 shows a diagram of the results of the test of samples V and III under a load of 500 g and under a load of 150 g.

The material combination in the samples V and III were tested under a load of 500 g and under a load of 150 g. The results from the measurements can be found in FIG. 5.

By means of performing measurements according to the examples above, the properties of different absorbent materials may be evaluated with regard to whether the materials swell or expand during wetting. On the basis of the measurements, it is thereafter possible to design absorbent structures which have essentially the same volume both in a wet state and in a dry state, and thus have very good shape permanence.

When designing absorbent structures intended for use in diapers or incontinence guards, it is convenient to use synthetic urine as testing liquid.

The material combinations which have been found to function well for the purpose are such where the height of the absorbent structure in a dry state constitutes between approximately 110% and 90% of the height in a wet state.

The invention should not be regarded as being limited to the herein mentioned examples and embodiments, instead a series of further variants and modifications are conceivable within the scope of the appended claims. For instance, a series of further material combinations may be used within the scope of the invention. Furthermore, all conceivable combinations of the described embodiments are intended to be embraced by the invention.

What is claimed is:

1. Absorbent structure for use in an absorbent article, the absorbent structure comprising:
    two different material types which are in direct or indirect contact with each other so that liquid may be transferred between the material types,
    wherein a first material type of said two different material types is constituted by material which swells when absorbing body fluid and a second material type of said two different material types is constituted by material which collapses when absorbing body fluid, and
    wherein a volume increase in the first material type is essentially equal to a volume reduction in the second material type when the absorbent structure is saturated with liquid, whereby the absorbent structure has a volume that is substantially the same both in a wet and in a dry state.

2. Absorbent article according to claim 1, wherein the volume of the absorbent structure in a dry state constitutes between approximately 110% and 90% of the volume in a wet state.

3. Absorbent structure according to claim 1, wherein the absorbent structure is formed by at least two material layers whereby a first material layer primarily includes the first material type and a second material layer primarily includes the second material type.

4. Absorbent structure according to claim 1, wherein the absorbent structure primarily includes a mixture of absorbent material of the first material type and material of the second material type.

5. Absorbent article according to claim 1, wherein a shape of the absorbent structure is conserved by the volume of the absorbent structure being substantially the same both in the wet and in the dry state.

6. Absorbent article according to claim 1, wherein the absorbent structure defines a form retentive absorbent structure.

7. An absorbent article intended for female users, with such a shape and size that the absorbent article may be substantially accommodated in a crotch region of a pair of panties and having a longitudinal direction, a transverse direction and a thickness direction, the article comprising:

a liquid-pervious cover layer, a liquid-impervious cover layer, and an absorbent body arranged between the two cover layers wherein a hump is arranged at the liquid-pervious cover layer of the article, the hump comprising absorbent material of a first material type and absorbent material of a second material type, wherein the first material type is constituted by material which swells when absorbing body fluid and the second material type is constituted by material which collapses when absorbing body fluid, and wherein a volume increase in the first material type is essentially equal to volume reduction in the second material type when the hump is saturated with liquid, whereby the hump has a volume that is substantially the same both in a wet and in a dry state.

8. Absorbent article according to claim 7, wherein the hump is formed by a layered structure exhibiting layers of the first material type and layers of the second material type.

9. Absorbent article according to claim 8, wherein the layers are arranged parallel to the thickness direction of the article, substantially perpendicularly between the liquid-pervious cover layer of the article and the liquid-impervious cover layer.

10. Absorbent article according to claim 8, wherein the layers are stacked on each other parallel to the liquid-pervious cover layer.

11. Absorbent article according to claim 7, wherein a shape of the hump of the absorbent body is conserved by the volume of the hump being substantially the same both in the wet and in the dry state.

12. Absorbent article according to claim 7, wherein the hump of the absorbent body defines a form retentive hump.

* * * * *